US006605615B2

(12) United States Patent
Medina et al.

(10) Patent No.: US 6,605,615 B2
(45) Date of Patent: Aug. 12, 2003

(54) HYDRAZONES AND ANALOGS AS CHOLESTEROL LOWERING AGENTS

(75) Inventors: Julio C. Medina, San Carlos, CA (US); Hirohiko Hasegawa, Osaka (JP)

(73) Assignee: Tularik Inc., South San Francisco, CA (US)

(*) Notice: Subject to any disclaimer, the term of this patent is extended or adjusted under 35 U.S.C. 154(b) by 0 days.

(21) Appl. No.: 09/798,247

(22) Filed: Mar. 1, 2001

(65) Prior Publication Data

US 2001/0056096 A1 Dec. 27, 2001

Related U.S. Application Data

(60) Provisional application No. 60/186,249, filed on Mar. 1, 2000, and provisional application No. 60/186,047, filed on Mar. 1, 2000.

(51) Int. Cl.$^7$ .................... C07D 215/38; C07D 333/58; C07D 209/14; A61K 31/15; A61P 9/10
(52) U.S. Cl. ................ 514/311; 546/173; 546/168; 514/314
(58) Field of Search ................ 546/173, 168; 514/311, 314

(56) References Cited

U.S. PATENT DOCUMENTS

| 4,728,668 A | | 3/1988 | Chakraborty | |
| 5,977,108 A | * | 11/1999 | Kikuchi et al. | 514/249 |

FOREIGN PATENT DOCUMENTS

| EP | 0 382 076 A1 | 2/1990 | |
| EP | 0 451 653 A2 | 3/1991 | |
| EP | 0 889 032 A1 | 9/1997 | |
| JP | 130434 A | 5/1994 | |
| JP | 7316144 | 12/1995 | |
| WO | WO 93/08171 | 4/1993 | ......... A61K/31/505 |

OTHER PUBLICATIONS

CAS printout for Youssefyeh et al. Chem Abstract 106:176188, 1987.*
CAS printout for Hasaneen et al. Chem Abstract 125: 10739, 1996.*
Chemical Abstract—Database acession No. XP–002181833.
Chemical Abstract—Database Accession No. XP–002181834.
Chemical Abstract—Database Accession No. XP–002181835.
Chemical Abstract—Database Accession No. XP–002181832.

* cited by examiner

*Primary Examiner*—Richard L. Raymond
*Assistant Examiner*—Hong Liu
(74) *Attorney, Agent, or Firm*—Townsend and Townsend and Crew LLP

(57) ABSTRACT

Hydrazones and hydrazone analogs are provided which are useful as upregulators of LDL receptors and can be used in the treatment of hypercholesterolemia and related disorders and conditions.

38 Claims, No Drawings

HYDRAZONES AND ANALOGS AS CHOLESTEROL LOWERING AGENTS

CROSS-REFERENCES TO RELATED APPLICATIONS

This application claims the benefit of U.S. Application Ser. No. 60/186,047, filed Mar. 1, 2000, and U.S. Application Ser. No. 60/186,249, filed Mar. 1, 2000, the disclosures of which are incorporated by reference herein.

BACKGROUND OF THE INVENTION

Atherosclerosis is disease resulting from excess cholesterol accumulation in the arterial walls, which forms plaques that inhibit blood flow and promote clot formation, ultimately causing heart attacks, stroke and claudication. The principal source of these cholesterol deposits are low-density lipoprotein (LDL) particles that are present in the blood. There is a direct correlation between LDL concentration and plaque formation in the arteries. LDL concentration is itself largely regulated by the supply of active LDL cell surface receptors which bind LDL particles and translocate them from the blood into the cell interior. Accordingly, the regulation of LDL receptor expression provides an important therapeutic target.

Lipoprotein disorders have been previously called hyperlipoproteinemias and defined as elevation of a lipoprotein level above normal. Hyperlipoproteinemias result in elevations of cholesterol, triglycerides or both and are clinically important because of their contribution to atherosclerotic diseases and pancreatitis.

Lipoproteins are spherical macromolecular complexes of lipid and protein. The lipid constituents of lipoproteins are esterified and unesterified (free) cholesterol, triglycerides, and phospholipids. Lipoproteins transport cholesterol and triglycerides from sites of absorption and synthesis to sites of utilization. Cholesteryl ester and triglycerides are nonpolar and constitute the hydrophobic core of lipoproteins in varying proportions. The lipoprotein surface coat contains the polar constituents-free cholesterol, phospholipids, and apolipoproteins—that permit these particles to be miscible in plasma.

Cholesterol is used for the synthesis of bile acids in the liver, the manufacture and repair of cell membranes, and the synthesis of steroid hormones. There are both exogenous and endogenous sources of cholesterol. The average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation). The rate-limiting enzyme in endogenous cholesterol synthesis is 3-hydroxy-3-methylglutaryl coenzyme A (HMG-CoA) reductase. Triglycerides, which are nonpolar lipids consisting of a glycerol backbone and three fatty acids of varying length and degrees of saturation, are used for storage in adipose tissue and for energy.

Lipoproteins are classified into groups based upon size, density, electrophoretic mobility, and lipid and protein composition. Very low density lipoproteins (VLDL) are large, triglyceride-rich lipoproteins that are synthesized and secreted by hepatocytes. VLDL interacts with lipoprotein lipase in capillary endothelium, and the core triglycerides are hydrolyzed to provide fatty acids to adipose and muscle tissue. About half of the catabolized VLDL particles are taken up by hepatic LDL receptors and the other half remain in plasma, becoming intermediate-density lipoprotein. IDL is enriched in cholesteryl ester relative to triglyceride and is gradually converted by hepatic triglyceride lipase to the smaller, denser, cholesterol ester-rich LDL. As IDL is converted to LDL, apolipoprotein E becomes detached, and only one apolipoprotein remains, apo B-100.

LDL normally carries about 75 percent of the circulating cholesterol. Cellular LDL uptake is mediated by a glycoprotein receptor molecule that binds to apo B-100. Approximately 70 percent of LDL is cleared by receptor uptake, and the remainder is removed by a scavenger cell pathway using nonreceptor mechanisms. The LDL receptors span the thickness of the cell's plasma membrane and are clustered in specialized regions where the cell membrane is indented to form craters called coated pits. These pits invaginate to form coated vesicles, where LDL is separated from the receptor and delivered to a lysosome so that digestive enzymes can expose the cholesteryl ester and cleave the ester bond to form free cholesterol. The receptor is recycled to the cell surface.

As free cholesterol liberated from LDL accumulates within cells, there are three important metabolic consequences. First, there is a decrease in the synthesis of HMG-CoA reductase, the enzyme that controls the rate of de novo cholesterol synthesis by the cell. Second, there is activation of the enzyme acyl cholesterol acyltransferase (ACAT), which esterifies free cholesterol into cholesterol ester, the cell's storage form of cholesterol. Third, accumulation of cholesterol suppresses the cell's synthesis of new LDL receptors. This feedback mechanism reduces the cell's uptake of LDL from the circulation.

Lipoproteins play a central role in atherogenesis. This association with the most common cause of death in the developed world defines the principal clinical importance of hyperlipoproteinemias. Individuals with an elevated cholesterol level are at higher risk for atherosclerosis. Multiple lines of evidence, including epidemiological, autopsy, animal studies and clinical trials, have established that LDL is atherogenic and that the higher the LDL level, the greater the risk of atherosclerosis and its clinical manifestations. A certain level of LDL elevation appears to be a necessary factor in the development of atherosclerosis, although the process is modified by myriad other factors (e.g., blood pressure, tobacco use, blood glucose level, antioxidant level, clotting factors). Acute pancreatitis is another major clinical manifestation of dyslipoproteinemia. It is associated with chylomicronemia and elevated VLDL levels. Most patients with acute pancreatitis have triglyceride levels above 2,000 mg/dL, but a 1983 NIH consensus development conference recommended that prophylactic treatment of hypertriglyceridemia should begin when fasting levels exceed 500 mg/dL. The mechanism by which chylomicronemia and elevated VLDL cause pancreatitis is unclear. Pancreatic lipase may act on triglyceride in pancreatic capillaries, resulting in the formation of toxic fatty acids that cause inflammation.

Abundant evidence indicates that treatment of hyperlipoproteinemia will diminish or prevent atherosclerotic complications. In addition to a diet that maintains a normal body weight and minimizes concentrations of lipids in plasma, therapeutic agents that lower plasma concentrations of lipoproteins, either by diminishing the production of lipoproteins or by enhancing the efficiency of their removal from plasma, are clinically important.

The most promising class of drugs currently available for the treatment of hyperlipoproteinemia or hypercholesterolemia acts by inhibiting HMG-CoA reductase, the rate-limiting enzyme in endogenous cholesterol synthesis. Drugs of this class competitively inhibit the activity of the enzyme. Eventually, this inhibition leads to a decrease in the endogenous synthesis of cholesterol and by normal homeostatic mechanisms, plasma cholesterol is taken up by LDL receptors to restore the intracellular cholesterol balance.

Through both the release of precursors of LDL and receptor-mediated LDL uptake from the serum, liver cells play a critical role in maintaining serum cholesterol homeostasis. In both man and animal models, an inverse correlation appears to exist between liver LDL receptors and LDL-associated serum cholesterol levels. In general, higher hepatocyte receptor numbers result in lower LDL-associated serum cholesterol levels. Cholesterol released into hepatocytes can be stored as cholesteryl esters, converted into bile acids and released into the bile duct, or enter into an oxycholesterol pool. It is this oxycholesterol pool that is believed to be involved in end product repression of both the genes of the LDL receptor and enzymes involved in the cholesterol synthetic pathway.

Transcription of the LDL receptor gene is known to be repressed when cells have an excess supply of cholesterol, probably in the form of oxycholesterol. A DNA sequence in the LDL receptor promoter region, known as the sterol response element (SRE), appears to confer this sterol end product repression. This element has been extensively investigated (Brown, Goldstein and Russell, U.S. Pat. Nos. 4,745,060 and 4,935,363). The SRE can be inserted into genes that normally do not respond to cholesterol, conferring sterol end product repression of the chimeric gene. The exact mechanism of the repression is not understood. Brown and Goldstein have disclosed methods for employing the SRE in a screen for drugs capable of stimulating cells to synthesize LDL receptors (U.S. Pat. No. 4,935,363). It would be most desirable if the synthesis of LDL receptors could be upregulated at the level of gene expression. The upregulation of LDL receptor synthesis at this level offers the promise of resetting the level of serum cholesterol at a lower, and clinically more desirable, level. Presently, however, there are no cholesterol lowering drugs that are known to operate at the level of gene expression. The present invention describes methods and compounds that act to inhibit directly or indirectly the repression of the LDL receptor gene, resulting in induction of the LDL receptor on the surface of liver cells, facilitating LDL uptake, bile acid synthesis and secretion to remove cholesterol metabolites and hence the lowering of LDL-associated serum cholesterol levels.

Accordingly, it is one object of the present invention to provide compounds which directly or indirectly upregulate LDL receptor synthesis at the level of gene expression and are useful in the treatment of hypercholesterolemia or hyperlipoproteinemia.

A further object of the present invention is to provide therapeutic compositions for treating hypercholesterolemia, hyperlipidemia, and other disorders associated with abnormally high levels of lipoproteins, cholesterol or triglycerides.

Still further objects are to provide methods for upregulating LDL receptor synthesis, for lowering serum LDL cholesterol levels, and for inhibiting atherosclerosis.

Other objects, features and advantages will become apparent to those skilled in the art from the following description and claims.

SUMMARY OF THE INVENTION

The present invention provides compounds of formula (I):

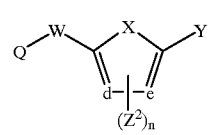

in which the lowercase letters d and e are each independently CH or N. The letter Q is $Ar^1C(R^1)=N-$ or

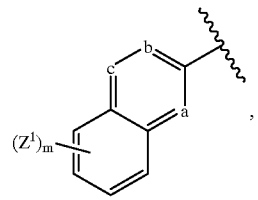

in which $Ar^1$ is substituted or unsubstituted aryl or substituted or unsubstituted heteroaryl, $R^1$ is H or substituted or unsubstituted $(C_1-C_4)$alkyl, the lowercase letters a, b and c are each independently CH or N, each $Z^1$ is independently selected from hydroxy, halogen, amino, nitro, cyano, substituted or unsubstituted monocyclic heterocycloalkyl, substituted or unsubstituted $(C_1-C_{10})$alkyl, substituted or unsubstituted $(C_1-C_{10})$alkoxy, substituted or unsubstituted benzyloxy, substituted or unsubstituted $(C_1-C_8)$acylamine, substituted or unsubstituted $(C_1-C_8)$alkylamine and substituted or unsubstituted di$(C_1-C_8)$alkylamine, and the subscript m is an integer of from 1 to 4. The letter W is NH, O, substituted or unsubstituted aryl or substituted or unsubstituted heteroaryl. The letter X represents S or —CH=CH—. The letter Y is —$CO_2R'$, —$CH_2OR'$, —C(O)R', —C(O)NR'R" or —$CH_2NR'R"$, wherein R' and R" are each independently hydrogen or $(C_1-C_8)$alkyl. Each $Z^2$ is independently hydroxy, halogen, amino, nitro, cyano, substituted or unsubstituted monocyclic heterocycloalkyl, substituted or unsubstituted $(C_1-C_{10})$alkyl, substituted or unsubstituted $(C_1-C_{10})$alkoxy, substituted or unsubstituted benzyloxy, substituted or unsubstituted $(C_1-C_8)$acylamine, substituted or unsubstituted $(C_1-C_8)$or substituted or unsubstituted di$(C_1-C_8)$alkylamine. The subscript n is an integer of from 1 to 2.

The invention also provides pharmaceutical compositions containing the foregoing compounds. The invention further provides methods of using the subject compounds and compositions for treating lipoprotein diseases and disorders, including, but not limited to, hyperlipoproteinemia, hypercholesterolemia and hyperlipidemia.

Unless otherwise indicated, the compounds provided in the above formula are meant to include pharmaceutically acceptable salts and prodrugs thereof.

Other objects, features and advantages of the present invention will become apparent to those skilled in the art from the following description and claims.

DESCRIPTION OF THE INVENTION

Definitions

The term "hypolipidemic agent" is meant to include any agent that lowers serum cholesterol, triglycerides or both. Such an agent may reduce the risk of diseases associated with elevated serum cholesterol and/or triglyceride levels, including atherosclerosis and pancreatitis. Exemplary hypolipidemic agents include, but are not limited to, LDL receptor expression modulators, bile acid sequestrants, nicotinic acid, HMG-CoA reductase inhibitors and fibric acid derivatives.

The terms "treat", "treating" and "treatment" refer to a method of alleviating or abrogating a disease and/or its attendant symptoms.

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multivalent radicals, having the number of carbon atoms designated (i.e, $C_1$–$C_6$ means one to six carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined below as heteroalkyl, alkylene, heteroalkylene, cycloalkyl and heterocycloalkyl. Typically, an alkyl group will have from 1 to 24 carbon atoms, with those groups having 10 or fewer carbon atoms being preferred in the present invention. The term "alkylene" by itself or as part of another substituent means a divalent radical derived from an alkane, as exemplified by —$CH_2CH_2CH_2CH_2$—. A "lower alkyl" or "lower alkylene" is a shorter chain alkyl or alkylene group, generally having eight or fewer carbon atoms.

The terms "alkoxy," "alkylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NR'R" wherein the R groups can be the same or different alkyl groups.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—H$_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

The term "acyl" refers to those groups derived from an organic acid by removal of the hydroxy portion of the acid. Accordingly, acyl is meant to include, for example, acetyl, propionyl, butyryl, decanoyl, pivaloyl and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The term "heteroaryl" is meant to include those aryl rings which contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy) propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR"R'R'", —OC(O)R', —C(O)R', —CO$_2$R', CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', S(O)$_2$R', —S(O)$_2$NR'R", —CN and —NO$_2$ in a number ranging from zero to (2N+1), where N is the total number of carbon atoms in such radical. R', R" and R'" each independently refer to hydrogen, unsubstituted (C$_1$–C$_8$)alkyl and heteroalkyl, unsubstituted aryl, aryl substituted with 1–3 halogens, unsubstituted alkyl, alkoxy or thioalkoxy groups, or aryl-(C$_1$–C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and are selected from: —halogen, —OR', —OC(O)R', —NR'R", —SR', —R', —CN, —NO$_2$— —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R', R" and R'" are independently selected from hydrogen, (C$_1$–C$_8$)alkyl and heteroalkyl, unsubstituted aryl, (unsubstituted aryl)-(C$_1$–C$_4$)alkyl, and (unsubstituted aryl)oxy-(C$_1$–C$_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and the subscript q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'—and —S(O)$_2$NR'— is selected from hydrogen or unsubstituted (C$_1$–C$_6$)alkyl.

As used herein, the term "heteroatom" is meant to include oxygen (0), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) *J. Pharm. Sci.*66:1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

DESCRIPTION OF THE EMBODIMENTS

In one aspect, the present invention provides compounds of general formula (I):

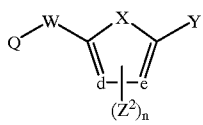

I wherein the lowercase letters d and e are each independently CH or N. The letter Q is $Ar^1C(R^1)=N-$ or

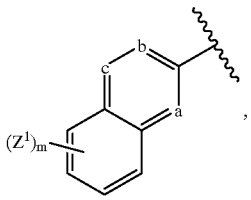

wherein $Ar^1$ is substituted or unsubstituted aryl or substituted or unsubstituted heteroaryl; $R^1$ is H or substituted or unsubstituted ($C_1$–$C_4$)alkyl; the lowercase letters a, b and c are each independently CH or N; each $Z^1$ is independently selected from hydroxy, halogen, amino, nitro, cyano, substituted or unsubstituted monocyclic heterocycloalkyl, substituted or unsubstituted ($C_1$–$C_{10}$)alkyl, substituted or unsubstituted ($C_1$–$C_{10}$)alkoxy, substituted or unsubstituted benzyloxy, substituted or unsubstituted ($C_1$–$C_8$)acylamine, substituted or unsubstituted ($C_1$–$C_8$)alkylamine and substituted or unsubstituted di($C_1$–$C_8$)alkylamine; and the subscript m is an integer of from 1 to 4. The letter W is NH, O, substituted or unsubstituted aryl or substituted or unsubstituted heteroaryl; X is S or —CH=CH—; Y is —$CO_2$R', —$CH_2$OR', —C(O)R', —C(O)NR'R" or —$CH_2$NR'R", wherein R' and R" are each independently hydrogen or ($C_1$–$C_8$)alkyl. Each $Z^2$ is independently hydroxy, halogen, amino, nitro, cyano, substituted or unsubstituted monocyclic heterocycloalkyl, substituted or unsubstituted ($C_1$–$C_{10}$) alkyl, substituted or unsubstituted ($C_1$–$C_{10}$)alkoxy, substituted or unsubstituted benzyloxy, substituted or unsubstituted ($C_1$–$C_8$)acylamine, substituted or unsubstituted ($C_1$–$C_8$)or substituted or unsubstituted di($C_1$–$C_8$) alkylamine. The subscript n is an integer of from 1 to 2.

In this aspect of the invention, Y is preferably —$CO_2$R' or —C(O)NR'R", more preferably —COOH. In other preferred embodiments, X is —CH=CH—. Particularly preferred embodiments are those in which Y is —$CO_2$R' or —C(O)NR'R", more preferably —COOH, and X is —CH=CH—.

In a preferred embodiment, Y is —$CO_2$R' or —C(O)NR'R", more preferably —COOH, X is —CH=CH—, Q is $Ar^1C(R^1)=N-$ and W is NH or O.

Still further preferred are those embodiments in which Y is —$CO_2$R' or —C(O)NR'R", more preferably —COOH, X is —CH=CH—, Q is $Ar^1C(R^1)=N-$ and $Ar^1$ is substituted or unsubstituted naphthyl, substituted or unsubstituted quinolinyl, substituted or unsubstituted benzothienyl, substituted or unsubstituted indolyl, substituted or unsubstituted benzofuranyl, substituted or unsubstituted furanyl, substituted or unsubstituted phenyl, substituted or unsubstituted pyrrolyl, and substituted or unsubstituted thienyl, substituted or unsubstituted naphthyridinyl, substituted or unsubstituted quinazolinyl, substituted or unsubstituted benzoimidazolyl, substituted or unsubstituted indolizinyl, substituted or unsubstituted quinoxalinyl, and substituted or unsubstituted pteridinyl.

A variety of substituents are useful for the aromatic groups provided above ($Ar^1$). Particularly preferred substituents are halogen, amino, unsubstituted ($C_1$–$C_6$)alkyl, ($C_1$–$C_6$)alkoxy, ($C_1$–$C_6$)haloalkyl, ($C_1$–$C_6$)haloalkoxy, phenyl, ($C_1$–$C_6$)haloalkylphenyl, phenoxy, benzyloxy, hydroxy($C_1$–$C_6$)alkyl, ($C_1$–$C_6$)acylamino and mono or di($C_1$–$C_6$)alkylamino. One of skill in the art will understand that the term "di($C_1$–$C_6$)alkylamino" includes those groups in which the alkyl portions are the same or different (e.g., ethyl methyl amino, isopropyl ethyl amino, ethyl propylamino, and the like).

In particularly preferred embodiments, W is NH, Y is —$CO_2$R' or —C(O)NR'R", more preferably —COOH, X is —CH=CH—, Q is $Ar^1$ C($R^1$)=N— and $R^1$ is H. In still further preferred embodiments, W is NH, Y is —$CO_2$R' or —C(O)NR'R", more preferably —COOH, X is —CH=CH—, Q is $Ar^1$ C($R^1$)=N—, $R^1$ is H and $Ar^1$ is substituted or unsubstituted naphthyl, substituted or unsubstituted quinolinyl, substituted or unsubstituted benzothienyl, substituted or unsubstituted indolyl, substituted or unsubstituted benzofuranyl, substituted or unsubstituted furanyl, substituted or unsubstituted phenyl, substituted or unsubstituted pyrrolyl, and substituted or unsubstituted thienyl, substituted or unsubstituted naphthyridinyl, substituted or unsubstituted quinazolinyl, substituted or unsubstituted benzoimidazolyl, substituted or unsubstituted indolizinyl, substituted or unsubstituted quinoxalinyl, and substituted or unsubstituted pteridinyl, wherein the substituents are each independently selected from halogen, amino, ($C_1$–$C_6$)alkyl, ($C_1$–$C_6$)alkoxy, ($C_1$–$C_6$)haloalkyl, ($C_1$–$C_6$)haloalkoxy, phenyl, ($C_1$–$C_6$) haloalkylphenyl, phenoxy, benzyloxy, hydroxy($C_1$–$C_6$) alkyl, ($C_1$–$C_6$)acylamino or mono or di($C_1$–$C_6$)alkylamino.

In still further preferred embodiments, W is NH, Y is —$CO_2$R' or —C(O)NR'R", more preferably —COOH, X is —CH=CH—, Q is $Ar^1C(R^1)=N-$, $R^1$ is H and $Ar^1$ is substituted or unsubstituted naphthyl, substituted or unsubstituted quinolinyl, substituted or unsubstituted benzothienyl, substituted or unsubstituted indolyl, substituted or unsubstituted benzofuranyl, substituted or unsubstituted furanyl, substituted or unsubstituted phenyl, substituted or unsubstituted pyrrolyl, and substituted or unsubstituted thienyl, substituted or unsubstituted naphthyridinyl, substituted or unsubstituted quinazolinyl, substituted or unsubstituted indolizinyl, and substituted or unsubstituted quinoxalinyl, wherein the substituents are each independently selected from halogen, amino, ($C_1$–$C_6$) alkyl, ($C_1$–$C_6$)alkoxy, ($C_1$–$C_6$)haloalkyl, ($C_1$–$C_6$) haloalkoxy, phenyl, ($C_1$–$C_6$)haloalkylphenyl, phenoxy, benzyloxy, hydroxy($C_1$–$C_6$)alkyl, ($C_1$–$C_6$)acylamino or mono or di($C_1$–$C_6$)alkylamino.

In another preferred embodiment, Y is —$CO_2$R' or —C(O)NR'R", more preferably —COOH, X is —CH=CH—, Q is

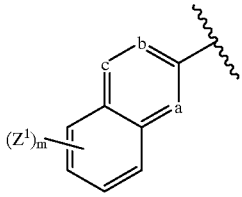

and W is substituted or unsubstituted aryl or substituted or unsubstituted heteroaryl.

Still farther preferred are those embodiments in which Y is —CO$_2$R' or —C(O)NR'R", more preferably —COOH, X is —CH=CH—, Q is

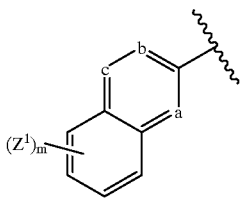

and W is selected from the group consisting of substituted or unsubstituted furanyl, substituted or unsubstituted phenyl, substituted or unsubstituted pyridyl, substituted or unsubstituted pyrazinyl, substituted or unsubstituted pyrrolyl, substituted or unsubstituted pyrimidinyl, substituted or unsubstituted triazinyl, substituted or unsubstituted imidazolyl, substituted or unsubstituted pyridazinyl, and substituted or unsubstituted thienyl.

Still further preferred are those embodiments in which Q is

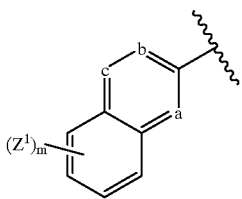

and each of $Z^1$ and $Z^2$ substituents are independently selected from halogen, amino, (C$_1$–C$_6$)alkyl, (C$_1$–C$_6$)alkoxy, (C$_1$–C$_6$)haloalkyl, (C$_1$–C$_6$)haloalkoxy, phenyl, (C$_1$–C$_6$)haloalkylphenyl, phenoxy, benzyloxy, hydroxy (C$_1$–C$_6$)alkyl, (C$_1$–C$_6$)acylamino and mono or di(C$_1$–C$_6$) alkylamino.

In another group of preferred embodiments, d and e are each CH, Q is

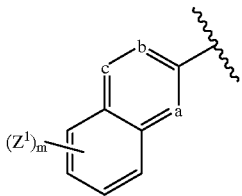

and one of a, b or c is N. More preferably, a is N and b, c, d and e are each CH. Within this group of embodiments, preferred groups for W, X, Y, $Z^1$ and $Z^2$ are the same as those provided above.

In another aspect, the present invention provides compounds having the formula (II):

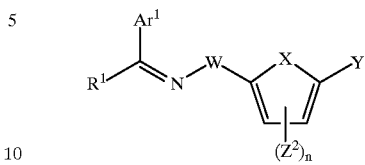

wherein; Ar$^1$ is substituted or unsubstituted aryl or substituted or unsubstituted heteroaryl; R$^1$ is H or substituted or unsubstituted (C$_1$–C$_4$)alkyl; W is NH, O, substituted or unsubstituted aryl or substituted or unsubstituted heteroaryl, X is S or —CH=CH—; Y is —CO$_2$R', —CH$_2$OR', —C(O) R', —C(O)NR'R" or —CH$_2$NR'R", wherein R' and R" are each independently hydrogen or (C$_1$–C$_8$)alkyl; each $Z^2$ is independently hydroxy, halogen, amino, nitro, cyano, substituted or unsubstituted monocyclic heterocycloalkyl, substituted or unsubstituted (C$_1$–C$_{10}$)alkyl, substituted or unsubstituted (C$_1$–C$_{10}$)alkoxy, substituted or unsubstituted benzyloxy, substituted or unsubstituted (C$_1$–C$_8$)acylamine, substituted or unsubstituted (C$_1$–C$_8$)or substituted or unsubstituted di(C$_1$–C$_8$)alkylamine and the subscript n is an integer of from 1 to 2.

In this aspect of the invention, Y is preferably —CO$_2$R' or —C(O)NR'R", more preferably —COOH. In other preferred embodiments, X is —CH=CH—. Particularly preferred embodiments are those in which Y is —CO$_2$R' or —C(O) NR'R", more preferably —COOH, and X is —CH=CH—.

In a preferred embodiment, Y is —CO$_2$R' or —C(O) NR'R", more preferably —COOH, X is —CH=CH—, and Ar$^1$ is substituted or unsubstituted naphthyl, substituted or unsubstituted quinolinyl, substituted or unsubstituted benzothienyl, substituted or unsubstituted indolyl, substituted or unsubstituted benzofuranyl, substituted or unsubstituted furanyl, substituted or unsubstituted phenyl, substituted or unsubstituted pyrrolyl, and substituted or unsubstituted thienyl, substituted or unsubstituted naphthyridinyl, substituted or unsubstituted quinazolinyl, substituted or unsubstituted benzoimidazolyl, substituted or unsubstituted indolizinyl, substituted or unsubstituted quinoxalinyl, and substituted or unsubstituted pteridinyl.

A variety of substituents are useful for the aromatic groups provided above (Ar$^1$). Particularly preferred substituents are halogen, amino, unsubstituted (C$_1$–C$_6$)alkyl, (C$_1$–C$_6$)alkoxy, (C$_1$–C$_6$)haloalkyl, (C$_1$–C$_6$)haloalkoxy, phenyl, (C$_1$–C$_6$)haloalkylphenyl, phenoxy, benzyloxy, hydroxy(C$_1$–C$_6$)alkyl, (C$_1$–C$_6$)acylamino and mono or di(C$_1$–C$_6$)alkylamino. One of skill in the art will understand that the term "di(C$_1$–C$_6$)alkylamino" includes those groups in which the alkyl portions are the same or different (e.g., ethyl methyl amino, isopropyl ethyl amino, ethyl propylamino, and the like).

In particularly preferred embodiments, R$^1$ is H, W is NH, X is —CH=CH— and Y is —CO$_2$R' or —C(O)NR'R", more preferably —COOH. In still further preferred embodiments, R$^1$ is H, W is NH, X is —CH=CH—, Y is —CO$_2$R' or —C(O)NR'R", more preferably —COOH, and Ar$^1$ is substituted or unsubstituted naphthyl, substituted or unsubstituted quinolinyl, substituted or unsubstituted benzothienyl, substituted or unsubstituted indolyl, substituted or unsubstituted benzofuranyl, substituted or unsubstituted furanyl, substituted or unsubstituted phenyl, substituted or unsubstituted pyrrolyl, and substituted or unsubstituted thienyl, substituted or unsubstituted naphthyridinyl, substituted or unsubstituted quinazolinyl, substituted or unsubstituted benzoimidazolyl, substituted or unsubstituted indolizinyl, substituted or unsubstituted quinoxalinyl, and substituted or unsubstituted pteridinyl, wherein the substituents are each independently selected from halogen, amino, $(C_1-C_6)$alkyl, $(C_1-C_6)$alkoxy, $(C_1-C_6)$haloalkyl, $(C_1-C_6)$haloalkoxy, phenyl, $(C_1-C_6)$haloalkylphenyl, phenoxy, benzyloxy, hydroxy$(C_1-C_6)$alkyl, $(C_1-C_6)$acylamino or mono or di$(C_1-C_6)$alkylamino.

In still further preferred embodiments, $R^1$ is H, W is NH, X is —CH=CH—, Y is —CO$_2$R' or —C(O)NR'R", more preferably —COOH, and $Ar^1$ is substituted or unsubstituted naphthyl, substituted or unsubstituted quinolinyl, substituted or unsubstituted benzothienyl, substituted or unsubstituted indolyl, substituted or unsubstituted benzofuranyl, substituted or unsubstituted furanyl, substituted or unsubstituted phenyl, substituted or unsubstituted pyrrolyl, and substituted or unsubstituted thienyl, substituted or unsubstituted naphthyridinyl, substituted or unsubstituted quinazolinyl, substituted or unsubstituted indolizinyl, and substituted or unsubstituted quinoxalinyl, wherein the substituents are each independently selected from halogen, amino, $(C_1-C_6)$alkyl, $(C_1-C_6)$alkoxy, $(C_1-C_6)$haloalkyl, $(C_1-C_6)$haloalkoxy, phenyl, $(C_1-C_6)$haloalkylphenyl, phenoxy, benzyloxy, hydroxy$(C_1-C_6)$alkyl, $(C_1-C_6)$acylamino or mono or di$(C_1-C_6)$alkylamino.

In a further aspect, the invention provides compounds having the formula (III):

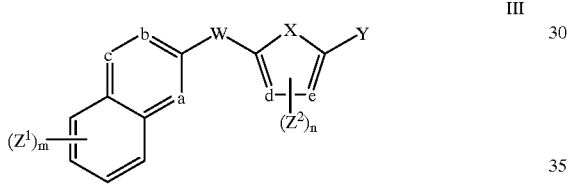

wherein the subscript m is an integer of from 1 to 4; the subscript n is an integer of from 1 to 2; the lowercase letters a, b, c, d and e are each independently CH or N; W is a substituted or unsubstituted aryl or substituted or unsubstituted heteroaryl group; X is S or —CH=CH—; Y is —CO$_2$R', —CH$_2$OR', —C(O)R', —C(O)NR'R" or —CH$_2$NR'R", wherein R' and R" are each independently hydrogen or $(C_1-C_8)$alkyl; and each $Z^1$ and $Z^2$ is independently selected from hydroxy, halogen, amino, nitro, cyano, substituted or unsubstituted monocyclic heterocycloalkyl, substituted or unsubstituted $(C_1-C_{10})$alkyl, substituted or unsubstituted $(C_1-C_{10})$alkoxy, substituted or unsubstituted benzyloxy, substituted or unsubstituted $(C_1-C_8)$acylamine, substituted or unsubstituted $(C_1-C_8)$alkylamine and substituted or unsubstituted di$(C_1-C_8)$alkylamine.

In preferred embodiments of this aspect of the invention, X is —CH=CH—. More preferably, X is —CH=CH— and Y is selected from —CO$_2$R' and —C(O)NR'R". Still more preferably, X is —CH=CH—, Y is selected from —CO$_2$R' and —C(O)NR'R" and W is selected from the group consisting of substituted or unsubstituted furanyl, substituted or unsubstituted phenyl, substituted or unsubstituted pyridyl, substituted or unsubstituted pyrazinyl, substituted or unsubstituted pyrrolyl, substituted or unsubstituted pyrimidinyl, substituted or unsubstituted triazinyl, substituted or unsubstituted imidazolyl, substituted or unsubstituted pyridazinyl, and substituted or unsubstituted thienyl. In the most preferred embodiments, Y is —COOH.

Still further preferred are those embodiments in which each of $Z^1$ and $Z^2$ substituents are independently selected from halogen, amino, $(C_1-C_6)$alkyl, $(C_1-C_6)$alkoxy, $(C_1-C_6)$haloalkyl, $(C_1-C_6)$haloalkoxy, phenyl, $(C_1-C_6)$haloalkylphenyl, phenoxy, benzyloxy, hydroxy$(C_1-C_6)$alkyl, $(C_1-C_6)$acylamino and mono or di$(C_1-C_6)$alkylamino.

In another group of preferred embodiments, d and e are each CH, and one of a, b or c is N. More preferably, a is N and b, c, d and e are each CH. Within this group of embodiments, preferred groups for W, X, Y, $Z^1$ and $Z^2$ are the same as those provided above.

Particularly preferred compounds of the present invention are selected from

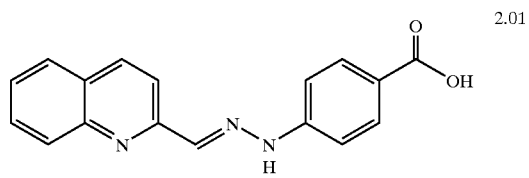
2.01

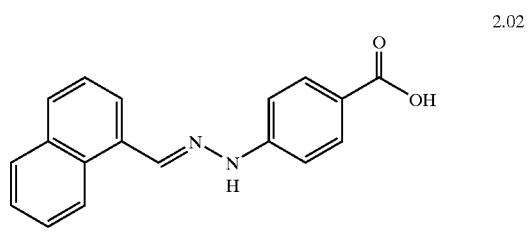
2.02

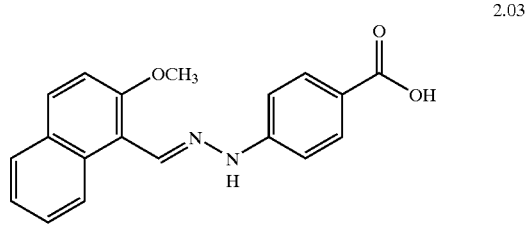
2.03

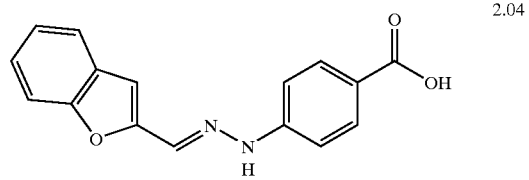
2.04

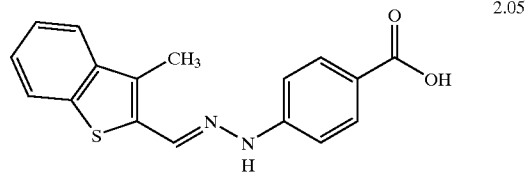
2.05

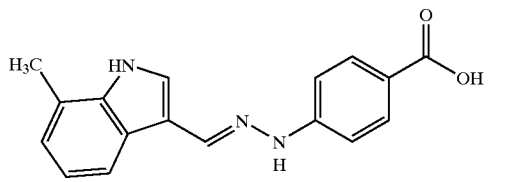
2.06

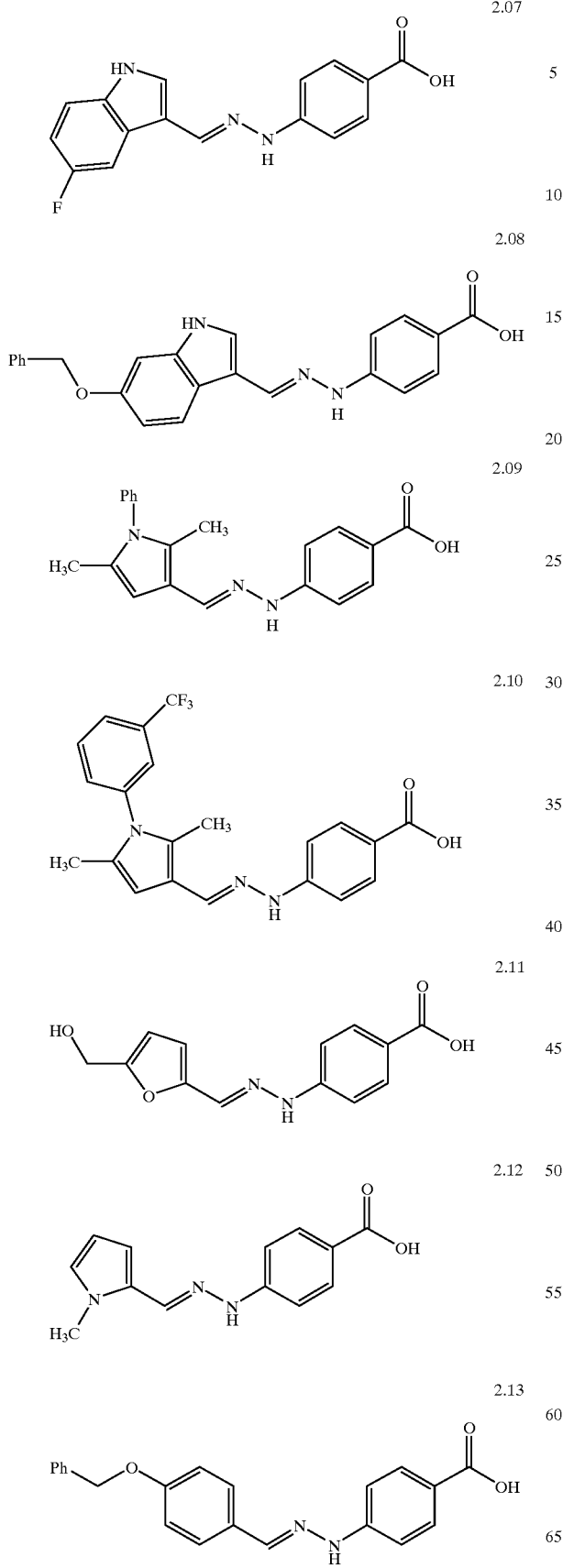
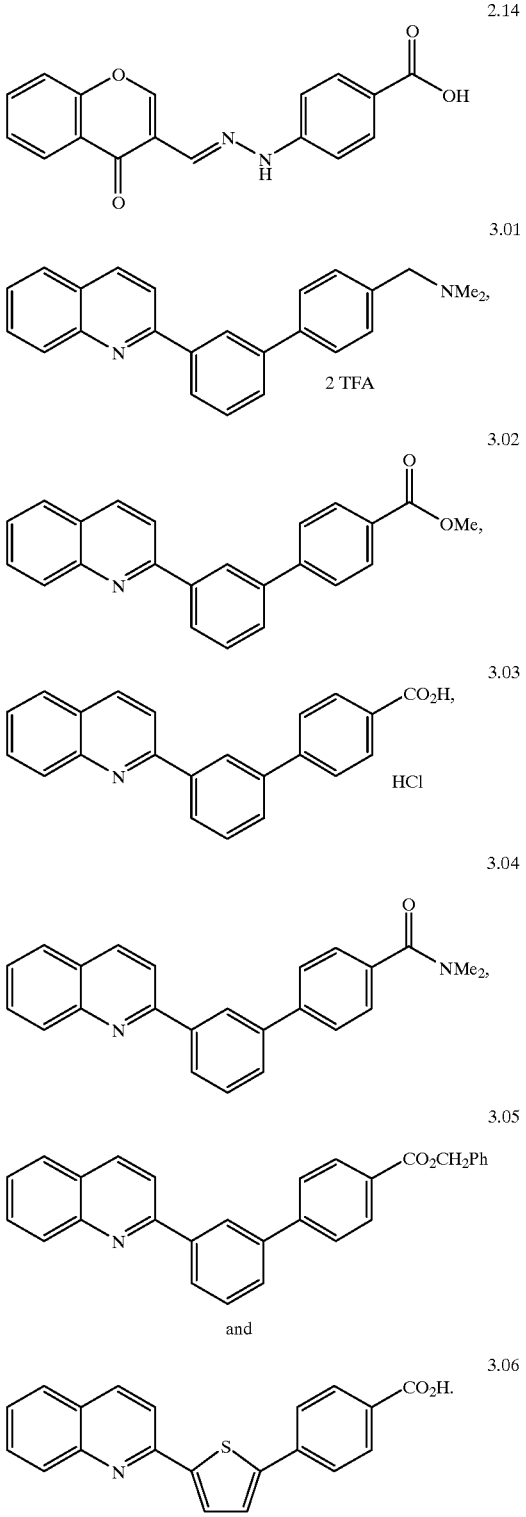
Synthesis of Hydrazones and Related Derivatives
Compounds of the present invention can be prepared using readily available materials or known intermediates. Scheme I provides a general scheme for the preparation of the diaryl hydrazones. According to this scheme, an aromatic aldehyde (or in other embodiments, an aromatic ketone) is combined with an aromatic hydrazine, typically under acidic conditions to form the diaryl hydrazones of the present invention.

SCHEME I

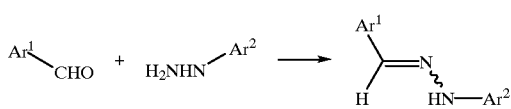

Alternatively, the compounds can be prepared as described in Example 2, using commercially available aldehydes and aryl hydrazines. Suitable aryl aldehydes and hydrazines can also be prepared as general described in March, Advanced Organic Chemistry, Second Edition, 1977, pages 221, 1167 and 1181.

Scheme II provides a general scheme for the preparation of triaryl compounds of the present invention. While the synthetic scheme is shown for compounds having at least two phenyl rings, the invention is not so limited and one of skill in the art will understand that related compounds can be prepared using suitable intermediates. According to this scheme, an aromatic orthoamino aldehyde is combined with 3-bromoacetophenone to provide the 2-(3-bromophenyl) quinoxaline (i, see J. Chem. Soc. (1959)1579) which is coupled with a substituted phenyl boronic acid (using Suzuki coupling conditions) to provide the triaryl compound (ii). Manipulation of the carboxylate moiety provides the derivatives (iii).

holesterolemic effects of compounds are known in the art. For example, compounds disclosed herein are shown to lower cholesterol levels in hamsters fed a high-cholesterol diet, using a protocol similar to that described in Spady et al. (1988) J. Clin. Invest. 81:300; Evans et al. (1994) J. Lipid Res. 35:1634; Lin et al (1995) J. Med. Chem. 38:277.

Combinatorial Libraries

Combinatorial libraries of compounds of the invention can be screened for pharmacological activity in in vitro or in vivo assays. Conventionally, new chemical entities with useful properties are generated by identifying a chemical compound (called a "lead compound") with some desirable property or activity, e.g., LDL receptor synthesis upregulating activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve conventional "lead compounds" or can themselves be used as potential or actual therapeutics.

SCHEME II

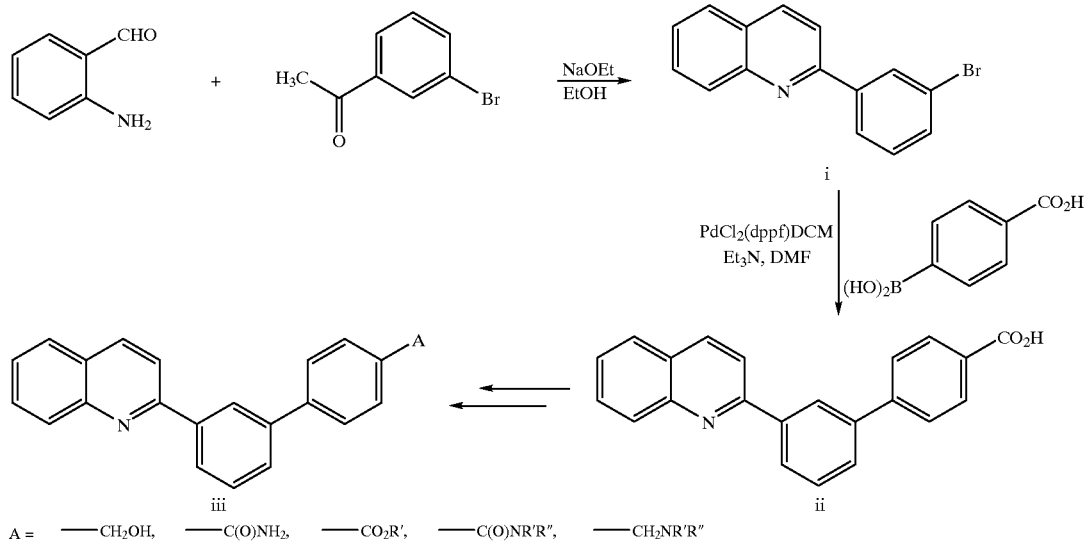

Evaluation of Compounds as Cholesterol Lowering Agents

The subject compositions were demonstrated to have pharmacological activity in in vitro and in vivo assays, e.g. are capable of specifically modulating a cellular physiology to reduce an associated pathology or provide or enhance a prophylaxis. Preferred compounds are capable of specifically regulating LDL receptor gene expression. Compounds may be evaluated in vitro for their ability to increase LDL receptor expression using western-blot analysis, for example, as described in Tarn et al. (1991) J. Biol. Chem. 266, 16764. Established animal models to evaluate hypoc- A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Millions of chemical compounds can be synthesized through such combinatorial mixing of chemical building blocks (Gallop et. al. (1994) J. Med. Chem. 37(9):1233–1251).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.* 37:487–493, Houghton et. al. (1991) *Nature* 354: 84–88), peptoid libraries (PCT Publication No WO 91/19735), encoded peptide libraries (PCT Publication WO 93/20242), random bio-oligomer libraries (PCT Publication WO 92/00091), benzodiazepine libraries (U.S. Pat. No. 5,288,514), libraries of diversomers, such as hydantoins, benzodiazepines and dipeptides (Hobbs et. al. (1993) *Proc. Nat. Acad. Sci. USA* 90:6909–6913), vinylogous polypeptide libraries (Hagihara et al. (1992) *J. Amer. Chem. Soc.* 114:6568), libraries of nonpeptidyl peptidomimetics with a Beta-D-Glucose scaffolding (Hirschmann et al. (1992) *J. Amer. Chem. Soc.* 114:9217–9218), analogous organic syntheses of small compound libraries (Chen et. al. (1994) *J. Am. Chem. Soc.* 116:2661), oligocarbamate libraries (Cho et al. (1993) *Science* 261:1303) and/or peptidyl phosphonate libraries (Campbell et al. (1994) *J. Org. Chem.* 59:658). See, generally, Gordon et al. (1994) *J. Med. Chem.* 37:1385–1401, nucleic acid libraries (see, e.g., Stratagene Corp.), peptide nucleic acid libraries (see, e.g., U.S. Pat. No. 5,539,083), antibody libraries (see, e.g., Vaughn et. al. (1996) *Nature Biotechnology* 14(3):309–314), and PCT/US96/10287), carbohydrate libraries (see, e.g., Liang et al. (1996) *Science* 274:1520–1522, and U.S. Pat. No. 5,593,853), and small organic molecule libraries (see, e.g., benzodiazepines, Baum (1993) *C&EN* January 18, page 33; isoprenoids, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 MPS, 390 MPS, Advanced Chem Tech, Louisville Ky.; Symphony, Rainin, Woburn Mass.; 433A Applied Biosystems, Foster City Calif.; 9050 Plus, Millipore, Bedford, Mass.).

A number of well known robotic systems have also been developed for solution phase chemistries. These systems includes automated workstations like the automated synthesis apparatus developed by Takeda Chemical Industries, LTD. (Osaka, Japan) and many robotic systems utilizing robotic arms (Zymate II, Zymark Corporation, Hopkinton Mass.; Orca, Hewlett-Packard, Palo Alto Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see e.g., ComGenex, Princeton N.J.; Asinex, Moscow, Russia; Tripos, Inc., St. Louis Mo.; ChemStar, Ltd, Moscow, Russia; 3D Pharmaceuticals, Exton Pa.; Martek Biosciences, Columbia Md.; etc.).

High Throughput Screening

High throughput assays for the presence, absence, quantification, or other properties of particular compounds may be used to test a combinatorial library that contains a large number of potential therapeutic compounds (potential modulator compounds). The assays are typically designed to screen large chemical libraries by automating the assay steps and providing compounds from any convenient source to assays, which are typically run in parallel (e.g., in microtiter formats on microtiter plates in robotic assays). Preferred assays detect enhancement or inhibition of LDL receptor synthesis.

High throughput screening systems are commercially available (see e.g., Zymark Corp., Hopkinton Mass.; Air Technical Industries, Mentor Ohio; Beckman Instruments, Inc., Fullerton Calif.; Precision Systems, Inc., Natick Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Compositions and Methods of Administration

In another aspect, the present invention provides pharmaceutical compositions comprising a pharmaceutically acceptable carrier and a compound as provided above, as well as methods for administering the subject compounds and compositions. Preferred compounds for use in the present compositions and methods are the same as those indicated above.

Accordingly, the invention provides methods of using the subject compounds and compositions to treat hypercholesterolemia, hyperlipidemia and other disorders associated with abnormally high levels of lipoproteins, cholesterol or triglycerides or provide medicinal prophylaxis, to upregulate LDL receptor gene expression in a cell, to reduce blood cholesterol concentration in a host, etc. These methods generally involve contacting the cell with or administering to the host or subject an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents or the present agents in other forms.

Accordingly, the invention further provides the subject compounds in the form of a prodrug, which can be metabolically converted to the subject compound by the recipient host. A wide variety of prodrug formulations are known in the art.

The compositions may be advantageously combined and/ or used in combination with other hypocholesterolemic and/or hypolipemic therapeutic or prophylactic agents, different from the subject compounds. In many instances, administration in conjunction with the subject compositions enhances the efficacy of such agents. Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, simvastatin, fluvastatin and lovastatin (Mevacor®); gemfibrozil and other fibric acids, such as gemfibrozil, clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to used labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and are not intended to limit the scope of the invention.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or as noted M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM $NH_4OAc$ in acetonitrile/water as delivery solvent.

Example 1

This example illustrates a method for the preparation of certain hydrazones.

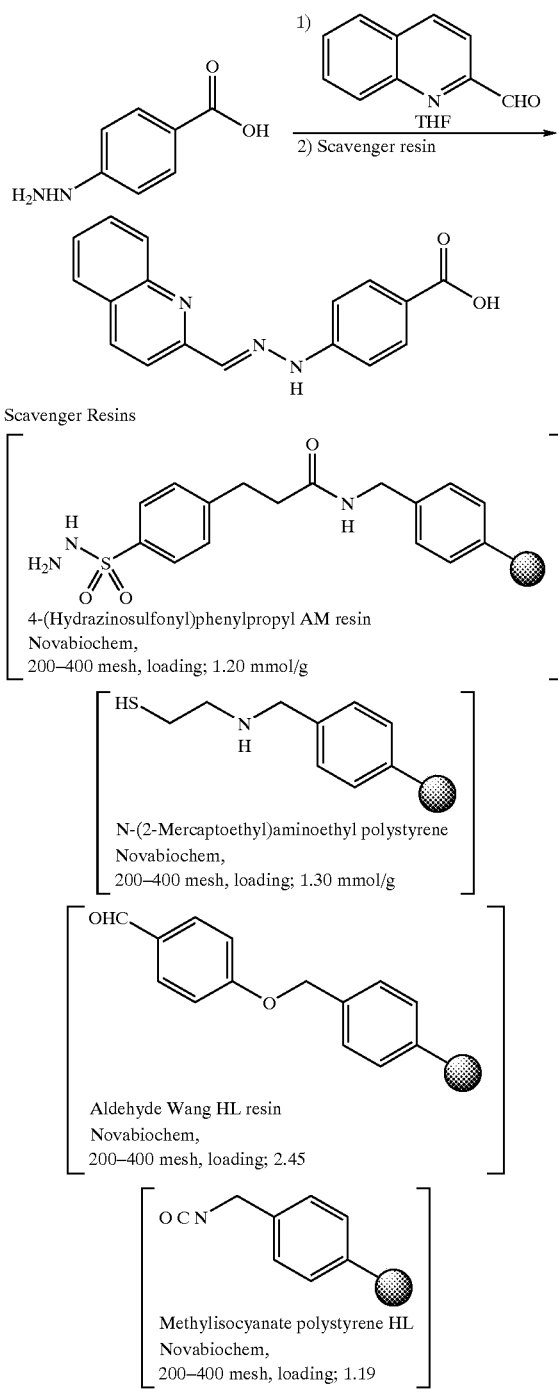

Scavenger Resins 4-(Hydrazinosulfonyl)phenylpropyl AM resin
Novabiochem,
200–400 mesh, loading; 1.20 mmol/g N-(2-Mercaptoethyl)aminoethyl polystyrene
Novabiochem,
200–400 mesh, loading; 1.30 mmol/g Aldehyde Wang HL resin
Novabiochem,
200–400 mesh, loading; 2.45

Methylisocyanate polystyrene HL
Novabiochem,
200–400 mesh, loading; 1.19

In this method, 4-hydrazinobenzoic acid (1.50 eq.) is placed in a 4.0 mL glass vial having a teflon screw-cap, along with quinoline-2-carboxaldehyde (1.00 eq.) and THF (4.0 mL). The vial is sealed with the teflon cap and agitated for 18–24 h at ambient temperature. Scavenger resin (Aldehyde Wang HL resin, 100 mg, 245 umol) is added and the resulting mixture is agitated for an additional 18–24 h at ambient temperature. The resulting mixture is filtered (using filtration tube PTFE from Whatman Inc.) and the filter is rinsed with THF. The filtrate is transferred to a 10 mL screw-cap glass vial (with teflon cap) containing N-(2-mercaptoethyl)aminoethyl polystyrene (150 mg, 195 umol). The resulting mixture is agitated for 18–24 h, then filtered and washed with THF. The combined filtrate and wash are concentrated. The residue is taken up in EtOAc-MeOH (9:1) and passed through a Sep-pack cartridge of silica gel. Concentration of the eluted portions provide the product.

Example 2

This example illustrates compounds prepared using the methods above and evaluated in the LDL-Receptor Western blot assay. Each of the compounds exhibited activity at 25 uM (++).

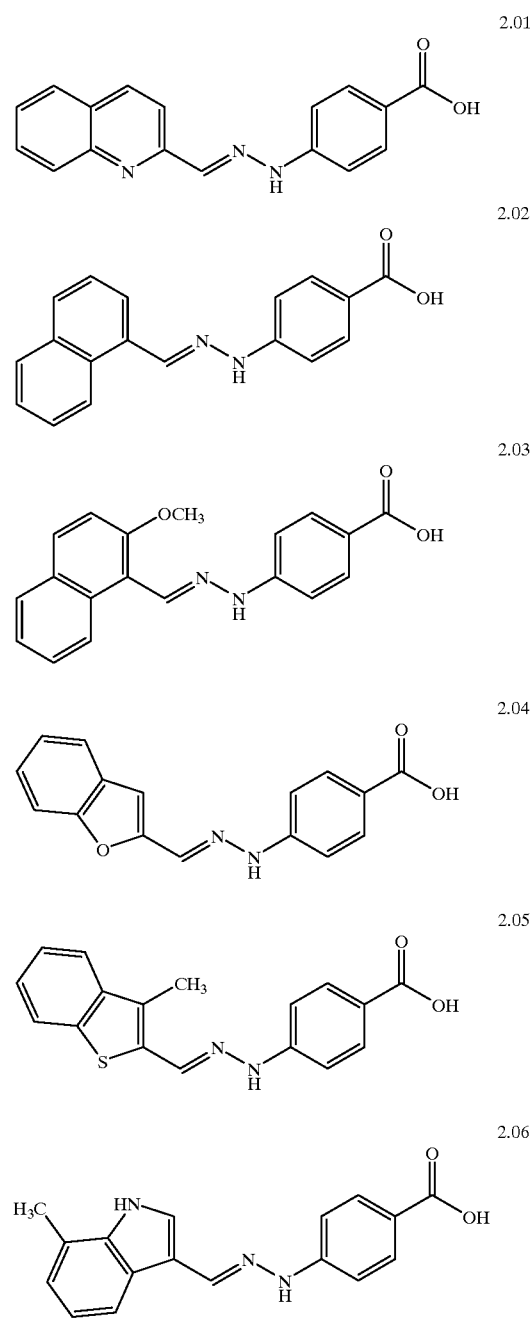

2.07
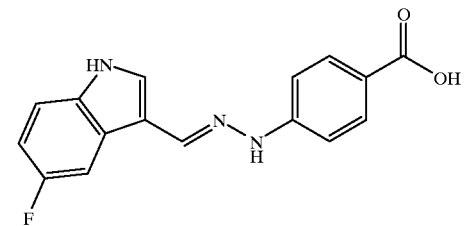

2.08
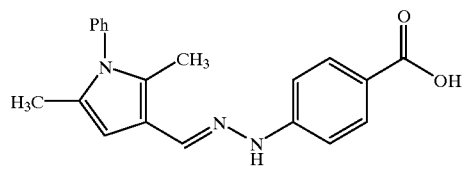

2.09
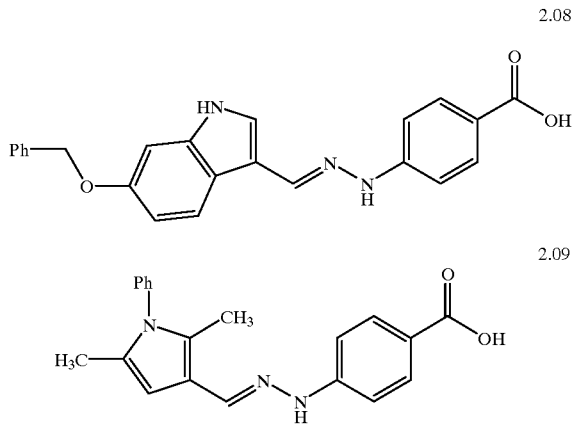

2.10
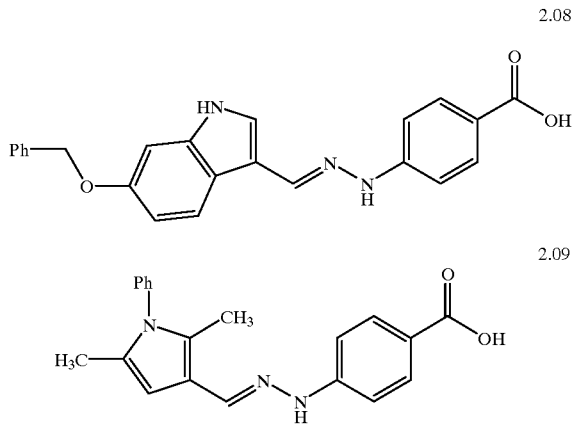

2.11
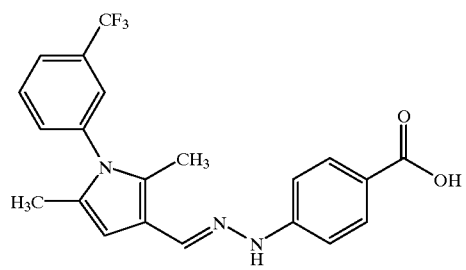

2.12
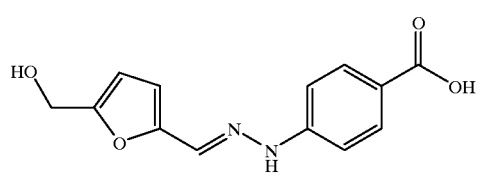

2.13
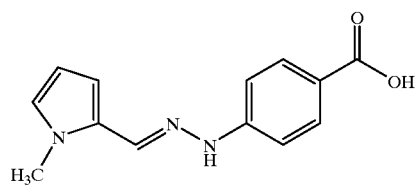

2.14
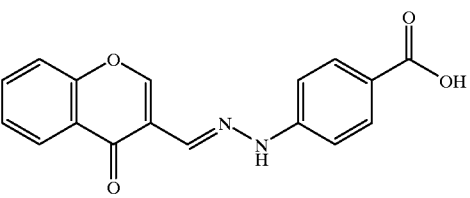

Representative analytical data is provided for selected compounds from the group above and additional compounds prepared by the methods described herein.

2.09
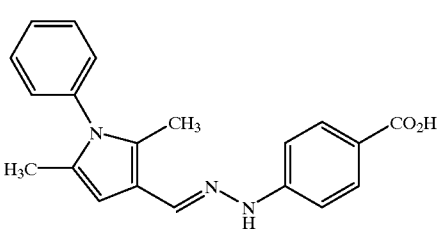

mp 204–206° C. $^1$H-NMR (DMSO-d$_6$) δ12.10 (1H, br s), 10.27 (1H, br s), 7.94 (1H, s), 7.75 (1H, m), 7.46–7.57 (3H, m), 7.31, (2H, m), 6.93 (2H, m), 6.25 (1H, s), 2.19 (3H, s), 2.09 (3H, s). MS(ES+) 334 (M+H, 100); MS(ES−) 332 (M−H, 100).

2.10
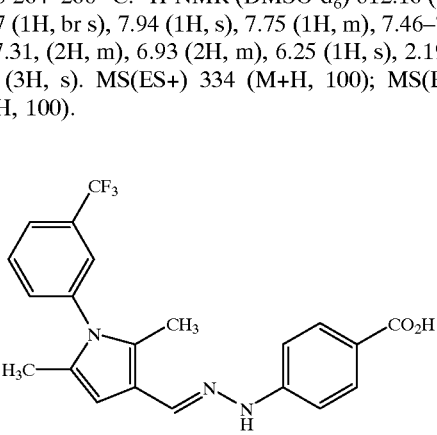

mp 170° C. $^1$H-NMR (DMSO-d$_6$) δ12.11 (1H, br s), 10.31 (1H, br s), 7.95 (1H, s), 7.86 (1H, m), 7.75–7.81 (4H, m), 7.68, (1H, m), 6.96 (1H, m), 6.29 (1H, s), 2.11 (3H, s), 2.00 (3H, s). MS(ES+) 402 (M+H, 100).

2.12
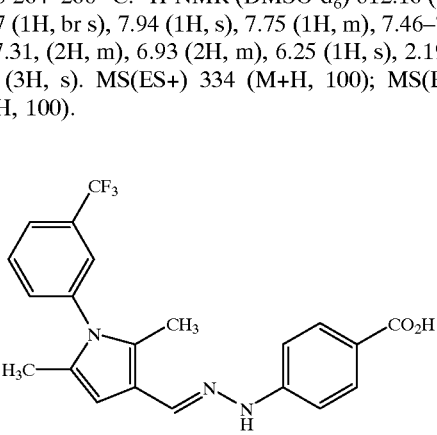

mp 202–204° C. $^1$H-NMR (DMSO-d$_6$) δ12.10 (1H, br s), 10.44 (1H, br s), 7.91 (1H, s), 7.78 (2H, d, J=8.9 Hz), 6.97 (2H, d, J=8.9 Hz), 6.88 (1H, t, J=2.2 Hz), 6.36 (1H, m), 6.08 (1H, m), 3.87 (3H, s). MS(ES+) 244 (M+22+H, 100).

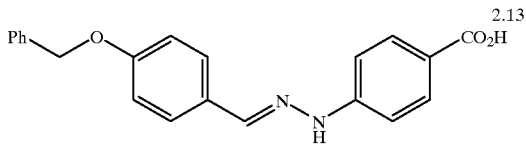
2.13

¹H-NMR (DMSO-d₆) δ12.2 (1H, br s), 10.65 (1H, br s), 7.90 (1H, s), 7.79 (2H, d, J=9.0 Hz), 7.62 (2H, d, J=8.9 Hz), 7.46 (2H, m), 7.40 (2H, m), 7.06 (4H, m), 5.14 (2H, s).

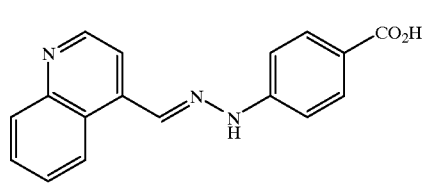
2.15

¹H-NMR (DMSO-d₆) δ12.28 (1H, br s), 11.32 (1H, s), 8.91 (1H, d, J=4.6 Hz), 8.65 (1H, m), 8.60 (1H, s), 8.07 (1H, m), 7.86–7.90 (3H, s), 7.81 (1H, m), 7.73 (1H, m), 7.23 (2H, m). MS(ES+) 292 (M+H, 100); MS(ES−) 290 (M−H, 100).

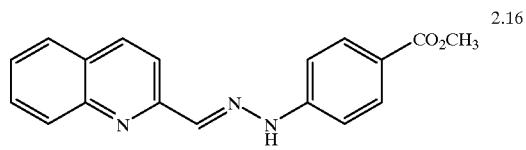
2.16 mp 209–211° C. ¹H-NMR (DMSO-d₆) δ11.34 (1H, s), 8.35 (1H, d, J=4.8 Hz), 8.17 (1H, d, J=8.8 Hz), 8.12 (1H, s), 7.98 (1H, m), 7.90 (2H, d, J=8.8 Hz), 7.76 (1H, m), 7.58 (1H, m), 7.26 (2H, d, J=8.8 Hz), 3.80 (3H, s). MS(ES+) 306 (M+H, 100); MS(ES−) 304 (M−H, 100).

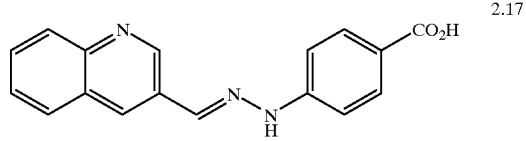
2.17 mp>250° C. ¹H-NMR (DMSO-d₆) δ12.25 (1H, br s), 11.08 (1H, s), 9.33 (1H, d, J=2.1 Hz), 8.50 (1H, d, J=1.9 Hz), 8.14 (1H, s), 8.02 (2H, m), 7.85 (2H, m), 7.75 (1H, m), 7.63 (1H, m), 7.20 (2H, d, J=8.8 Hz). MS(ES+) 292 (M+H, 100); MS(ES−) 290 (M−H, 100).

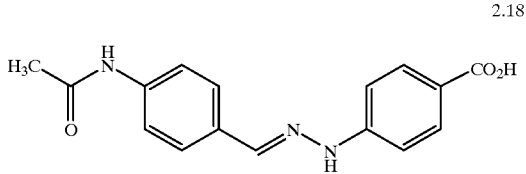
2.18 mp>250° C. ¹H-NMR (DMSO-d₆) δ12.22 (1H, br s), 10.70 (1H, s), 10.05 (1H, s), 7.89 (1H, s), 7.80 (2H, d, J=8.8 Hz), 7.61 (4H, m), 7.08 (2H, d, J=8.8 Hz). MS(ES+) 320 (M+22+H, 100); MS(ES−) 296 (M−H, 100).

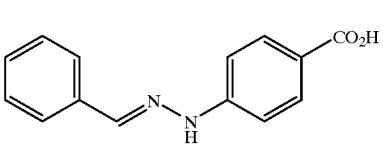
2.19 mp 217–219° C. ¹H-NMR (DMSO-d₆) δ12.28 (1H, br s), 10.80 (1H, s), 7.95 (1H, s), 7.81 (1H, d, J=8.8 Hz), 7.68 (1H, m), 7.41 (2H, m), 7.33 (1H, m), 7.11 (2H, d, J=8.8 Hz). MS(ES−) 239 (M−H, 100).

Example 3

This example provides structures and physical data for compounds of the present invention prepared according to the methods outlined in Scheme II. Each of the compounds provided below exhibited activity in the LDL-R western assay at 15 μM.

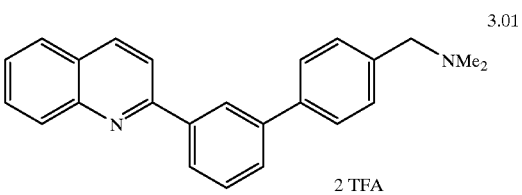
3.01 oil

¹H-NMR (DMSO-d₆) δ8.48–8.52 (2H, m), 8.26–8.30 (2H, m) 8.11 (1H, d, J=8.5 Hz), 8.03 (1H, m), 7.76–7.82 (4H, m), 7.60–7.67 (2H, m), 7.44 (2H, d, J=8.1 Hz). MS(ES+) 339 (M+H, 100).

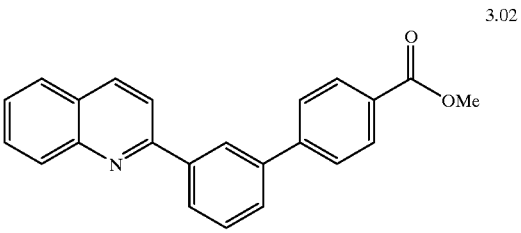
3.02 mp 109–112° C. ¹H-NMR (CDCl₃) δ8.46 (1H, m), 8.27 (1H, d, J=8.5 Hz), 8.15–8.23 (4H, m), 7.95 (1H, d, J=8.5 Hz), 7.82 (1H, d, J=8.0 Hz), 7.72–7.81 (4H, m), 7.64 (1H, t, J=7.7 Hz), 7.56 (1H, m), 3.97 (3H, s).

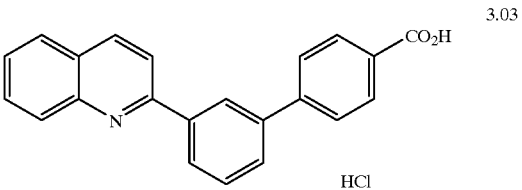
3.03 mp>250° C. ¹H-NMR (DMSO-d₆) δ8.64 (1H, d, J=8.7 Hz), 8.59 (1H, m), 8.37 (1H, d, J=8.7 Hz), 8.33 (1H, m), 8.20 (1H, d, J=8.6 Hz), 8.08–8.11 (3H, m), 7.83–7.95 (4H, m), 7.35–7.75 (2H, m). MS(ES+) 326 (M+H, 100); MS(ES−) 324 (M−H, 100).

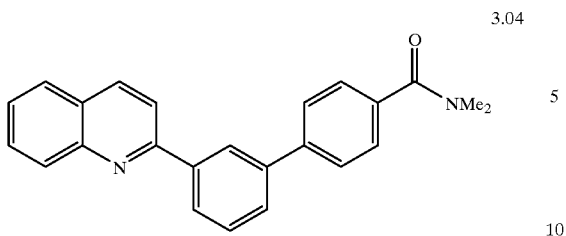

oil $^1$H-NMR (CDCl$_3$) δ8.43 (1H, m), 8.27 (1H, m), 8.16 (1H, m), 7.95 (1H, m), 7.86 (1H, m), 7.70–7.77 (4H, m), 7.54–7.64 (4H, m), 3.13 (3H, br s), 3.12 (3H, br s). MS (ES–) 353 (M–H, 100).

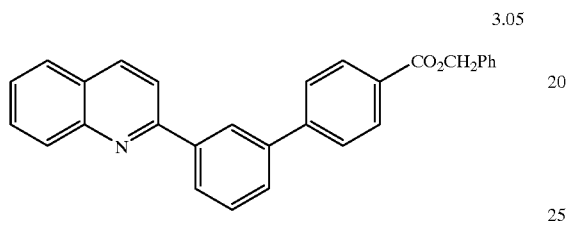

oil $^1$H-NMR (DMSO-d$_6$) δ8.59 (1H, m), 8.51 (1H, d, J=8.8 Hz), 8.29–8.36 (2H, m), 8.09–8.15 (4H, m), 7.97–8.04 (4H, m), 8.80 (1H, m), 7.81 (1H, m), 7.70 (1H, m), 7.62 (1H, m) 7.51 (1H, m), 7.37–7.45 (2H, m), 5.41 (2H, s). MS(ES+) 416 (M+H, 100).

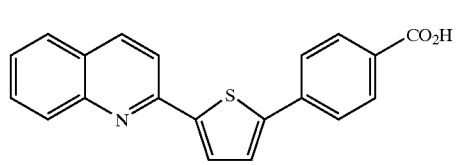

mp 176–178° C. MS (ES–) 330 (M–H, 100).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

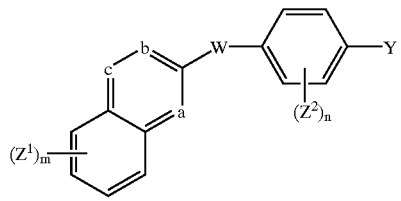

wherein
the subscript n is an integer of from 1 to 2;
the lowercase letters a, b and c are each independently CH or N with the proviso that only one of a, b or c is N, each $Z^1$ is independently selected from hydroxy, halogen, amino, nitro, cyano, substituted or unsubstituted 5 or 6 membered monocyclic heterocycloalkyl, substituted or unsubstituted ($C_1$–$C_{10}$)alkyl, substituted or unsubstituted ($C_1$–$C_{10}$) alkoxy, substituted or unsubstituted benzyloxy, substituted or unsubstituted ($C_1$–$C_8$)acylamine, substituted or unsubstituted ($C_1$–$C_8$)alkylamine and substituted or unsubstituted di($C_1$–$C_8$) alkylamine, and the subscript m is an integer of from 1 to 4;

W is substituted or unsubstituted aryl;

Y is a member selected from the group consisting of —CO$_2$R', —CH$_2$OR', —C(O)R', —C(O)NR'R" and —CH$_2$NR'R", wherein R' and R" are each members independently selected from the group consisting of hydrogen and ($C_1$–$C_8$)alkyl; and each $Z^2$ is a member independently selected from the group consisting of hydroxy, halogen, amino, nitro, cyano, substituted or unsubstituted monocyclic heterocycloalkyl, substituted or unsubstituted ($C_1$–$C_{10}$)alkyl, substituted or unsubstituted ($C_1$–$C_{10}$) alkoxy, substituted or unsubstituted benzyloxy, substituted or unsubstituted ($C_1$–$C_8$)acylamine, substituted or unsubstituted ($C_1$–$C_8$)alkylamine and substituted or unsubstituted di($C_1$–$C_8$)alkylamine.

2. The compound of claim 1, wherein W is unsubstituted aryl.

3. A compound of claim 1, wherein Y is selected from the group consisting of —CO$_2$R' and —C(O)NR'R".

4. A compound of claim 3, wherein W is substituted or unsubstituted phenyl.

5. A compound of claim 4, wherein each of said $Z^1$ and $Z^2$ substituents are independently selected from the group consisting of halogen, amino, ($C_1$–$C_6$)alkyl, ($C_1$–$C_6$)alkoxy, ($C_1$–$C_6$)haloalkyl, ($C_1$–$C_6$)haloalkoxy, phenyl, ($C_1$–$C_6$) haloalkylphenyl, phenoxy, benzyloxy, hydroxy($C_1$–$C_6$) alkyl, ($C_1$–$C_6$)acylamino and mono or di($C_1$–$C_6$) alkylamino.

6. A compound of claim 2, wherein a is N.

7. A compound of claim 1, wherein a is N.

8. A compound in accordance with claim 1, wherein a is N and W is substituted or unsubstituted phenyl.

9. A compound selected from the group consisting of

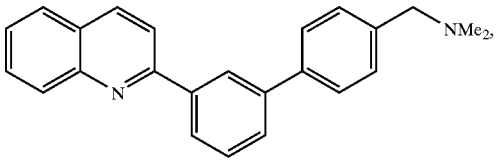

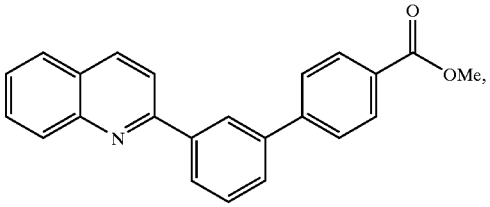

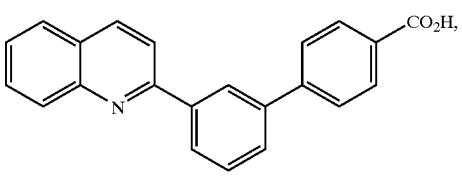

-continued

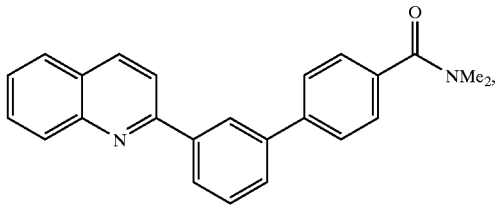

and

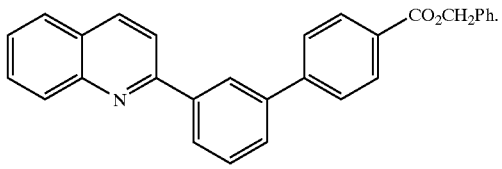

10. A pharmaceutical composition for lowering blood cholesterol, comprising a pharmaceutically acceptable excipient and a compound of the formula

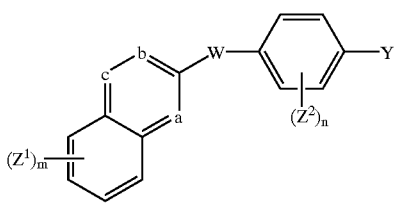

wherein
the subscript n is an integer of from 1 to 2;
the lowercase letters a, b and c are each independently CH or N with the proviso that only one of a, b or c is N, each $Z^1$ is independently selected from hydroxy, halogen, amino, nitro, cyano, substituted or unsubstituted monocyclic heterocycloalkyl, substituted or unsubstituted $(C_1-C_{10})$alkyl, substituted or unsubstituted $(C_1-C_{10})$alkoxy, substituted or unsubstituted benzyloxy, substituted or unsubstituted $(C_1-C_8)$acylamine, substituted or unsubstituted $(C_1-C_8)$alkylamine and substituted or unsubstituted di$(C_1-C_8)$alkylamine, and the subscript m is an integer of from 1 to 4;
W is substituted or unsubstituted aryl;
Y is a member selected from the group consisting of —$CO_2R'$, —$CH_2OR'$, —$C(O)R'$, —$C(O)NR'R''$ and —$CH_2NR'R''$, wherein R' and R'' are each members independently selected from the group consisting of hydrogen and $(C_1-C_8)$alkyl; and
each $Z^2$ is a member independently selected from the group consisting of hydroxy, halogen, amino, nitro, cyano, substituted or unsubstituted monocyclic heterocycloalkyl, substituted or unsubstituted $(C_1-C_{10})$alkyl, substituted or unsubstituted $(C_1-C_{10})$alkoxy, substituted or unsubstituted benzyloxy, substituted or unsubstituted $(C_1-C_8)$acylamine, substituted or unsubstituted $(C_1-C_8)$alkylamine and substituted or unsubstituted di$(C_1-C_8)$alkylamine.

11. A composition of claim 10, wherein W is unsubstituted aryl.

12. A composition in accordance with claim 10, wherein a is N and W is substituted or unsubstituted phenyl.

13. A composition of claim 10, wherein Y is selected from the group consisting of —$CO_2R'$ and —$C(O)NR'R''$.

14. A composition of claim 13, wherein W is substituted or unsubstituted phenyl.

15. A composition of claim 14, wherein each of said $Z^1$ and $Z^2$ substituents are independently selected from the group consisting of halogen, amino, $(C_1-C_6)$alkyl, $(C_1-C_6)$alkoxy, $(C_1-C_6)$haloalkyl, $(C_1-C_6)$haloalkoxy, phenyl, $(C_1-C_6)$haloalkylphenyl, phenoxy, benzyloxy, hydroxy $(C_1-C_6)$alkyl, $(C_1-C_6)$acylamino and mono or di$(C_1-C_6)$alkylamino.

16. A composition of claim 10, wherein a is N and W is unsubstituted phenyl.

17. A composition of claim 10, wherein a is N.

18. A composition comprising a pharmaceutically acceptable excipient and a compound selected from the group consisting of

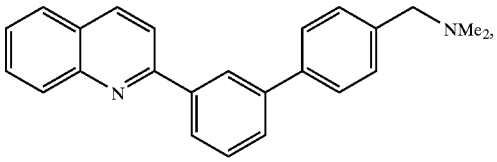

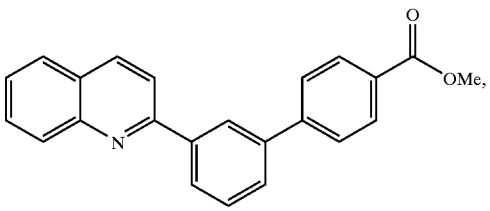

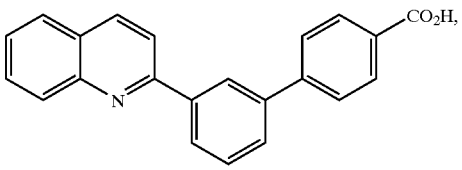

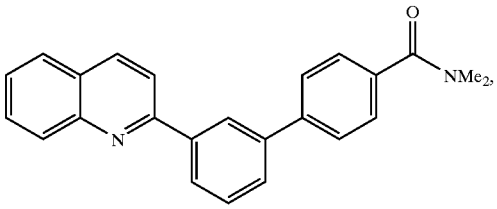

and

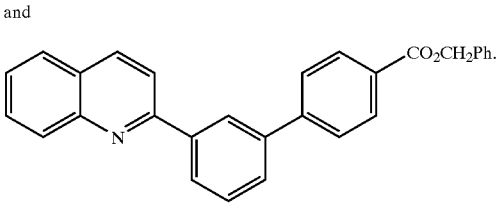

19. A composition in accordance with claim 10, further comprising a second hypolipidemic agent.

20. A composition in accordance with claim 19, wherein said second hypolipidemic agent is selected from the group consisting of bile acid sequestrants, nicotinic acid and its derivatives, HMG-CoA reductase inhibitors, fibric acids, probucol, raloxifene and its derivatives, and combinations thereof.

21. A composition in accordance with claim 11, further comprising a second hypolipidemic agent.

22. A composition in accordance with claim 18, further comprising a second hypolipidemic agent.

23. A composition in accordance with claim 10, wherein the composition is in unit dose format and has from 0.1 to 1000 mg of the compound per unit dose.

24. A composition in accordance with claim 10, wherein the composition is in unit dose format and has from 1 to 100 mg of the compound per unit dose.

25. A method of treating a disease or condition selected from the group consisting of hypercholesterolemia, hyperlipidemia and other metabolic disorders associated with abnormally high levels of lipoproteins, cholesterol or triglycerides, said method comprising administering to a subject in need of such treatment an effective amount of a compound having the formula:

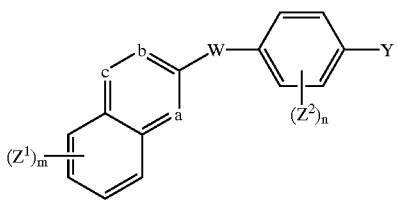

wherein
the subscript n is an integer of from 1 to 2;
the lowercase letters a, b and c are each independently CH or N with the proviso that only one of a, b or c is N, each $Z^1$ is independently selected from hydroxy, halogen, amino, nitro, cyano, substituted or unsubstituted monocyclic heterocycloalkyl, substituted or unsubstituted $(C_1-C_{10})$alkyl, substituted or unsubstituted $(C_1-C_{10})$alkoxy, substituted or unsubstituted benzyloxy, substituted or unsubstituted $(C_1-C_8)$acylamine, substituted or unsubstituted $(C_1-C_8)$alkylamine and substituted or unsubstituted di$(C_1-C_8)$alkylamine, and the subscript m is an integer of from 1 to 4;
W is substituted or unsubstituted aryl;
Y is a member selected from the group consisting of —$CO_2R'$, —$CH_2OR'$, —$C(O)R'$, —$C(O)NR'R''$ and —$CH_2NR'R''$, wherein R' and R'' are each members independently selected from the group consisting of hydrogen and $(C_1-C_8)$alkyl; and
each $Z^2$ is a member independently selected from the group consisting of hydroxy, halogen, amino, nitro, cyano, substituted or unsubstituted monocyclic heterocycloalkyl, substituted or unsubstituted $(C_1-C_{10})$alkyl, substituted or unsubstituted $(C_1-C_{10})$ alkoxy, substituted or unsubstituted benzyloxy, substituted or unsubstituted $(C_1-C_8)$acylamine, substituted or unsubstituted $(C_1-C_8)$alkylamine and substituted or unsubstituted di$(C_1-C_8)$alkylamine.

26. A method in accordance with claim 25, wherein W is unsubstituted aryl.

27. A method in accordance with claim 25, wherein a is N and W is substituted or unsubstituted phenyl.

28. A compound of claim 25, wherein Y is selected from the group consisting of —$CO_2R'$ and —$C(O)NR'R''$.

29. A method in accordance with claim 28, wherein W is substituted or unsubstituted phenyl.

30. A method in accordance with claim 29, wherein each of said $Z^1$ and $Z^2$ substituents are independently selected from the group consisting of halogen, amino, $(C_1-C_6)$alkyl, $(C_1-C_6)$alkoxy, $(C_1-C_6)$haloalkyl, $(C_1-C_6)$haloalkoxy, phenyl, $(C_1-C_6)$haloalkylphenyl, phenoxy, benzyloxy, hydroxy$(C_1-C_6)$alkyl, $(C_1-C_6)$acylamino and mono or di$(C_1-C_6)$alkylamino.

31. A method in accordance with claim 25, wherein a is N.

32. A method in accordance with claim 26, wherein a is N and W is unsubstituted phenyl.

33. A method of treating a disease or condition selected from the group consisting of hypercholesterolemia, hyperlipidemia and other metabolic disorders associated with abnormally high levels of lipoproteins, cholesterol or triglycerides, said method comprising administering to a subject in need of such treatment an effective amount of a compound selected from the group consisting of

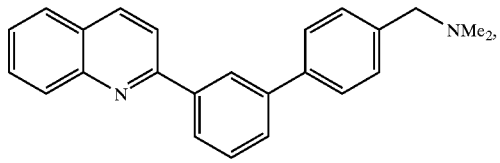

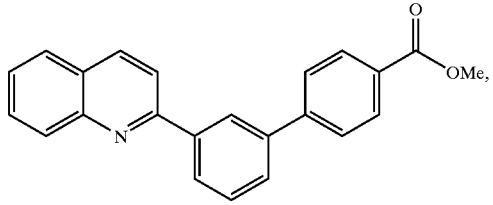

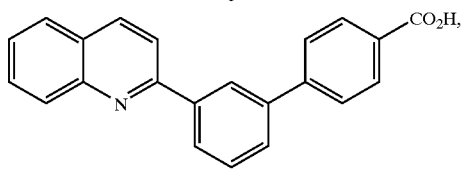

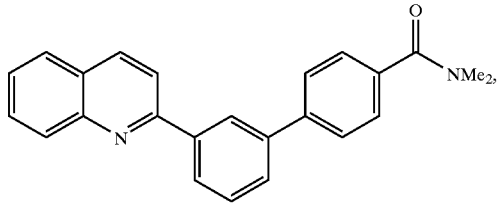

and

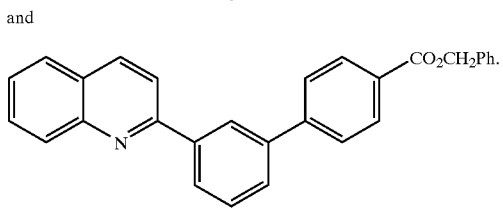

34. A method in accordance with claim 25, wherein said compound is administered in combination with a second hypolipidemic agent.

35. A method in accordance with claim 34, wherein said second hypolipidemic agent is selected from the group consisting of bile acid sequestrants, nicotinic acid and its derivatives, HMG-CoA reductase inhibitors, fibric acids, probucol, raloxifene and its derivatives, and combinations thereof.

36. A method in accordance with claim 28, wherein said compound is administered in combination with a second hypolipidemic agent.

37. A method in accordance with claim 26, wherein said compound is administered in combination with a second hypolipidemic agent.

38. A method in accordance with claim 25, wherein said compound and said second hypolipidemic agent are administered sequentially.

* * * * *

UNITED STATES PATENT AND TRADEMARK OFFICE
CERTIFICATE OF CORRECTION

PATENT NO. : 6,605,615 B2  Page 1 of 1
DATED : August 12, 2003
INVENTOR(S) : Julio C. Medina et al.

It is certified that error appears in the above-identified patent and that said Letters Patent is hereby corrected as shown below:

Column 33,
Line 52, kindly delete "compound of claim 25", and insert therefor -- method of claim 25 --

Signed and Sealed this

Twentieth Day of January, 2004

JON W. DUDAS
*Acting Director of the United States Patent and Trademark Office*